(12) United States Patent
Wu et al.

(10) Patent No.: US 6,475,154 B1
(45) Date of Patent: Nov. 5, 2002

(54) METHOD AND APPARATUS FOR NON-INVASIVE BLOOD-PRESSURE MEASUREMENT

(75) Inventors: Shu-Mei Wu, Taipei; Yao Ou-Yang, Jung he; Ja-Shi Wu, Kaohsiung; Tung-Chuang Jan; Chao-Wang Chen, both of Taipei, all of (TW)

(73) Assignee: Taidoc Corp., Ltd., Taipei (TW)

( * ) Notice: Subject to any disclaimer, the term of this patent is extended or adjusted under 35 U.S.C. 154(b) by 0 days.

(21) Appl. No.: 09/708,465

(22) Filed: Nov. 9, 2000

(51) Int. Cl.$^7$ ................................................ A61B 5/02

(52) U.S. Cl. ................... 600/494; 600/485; 600/490; 600/493

(58) Field of Search ................... 600/490, 493–496, 600/485

(56) References Cited

U.S. PATENT DOCUMENTS

| | | | | |
|---|---|---|---|---|
| 4,926,873 A | * | 5/1990 | Frankenreiter | 600/494 |
| 4,984,577 A | * | 1/1991 | Frankenreiter | 600/494 |
| 5,579,776 A | * | 12/1996 | Medero | 600/493 |
| 5,651,370 A | * | 7/1997 | Hersh et al. | 600/494 |

\* cited by examiner

Primary Examiner—Robert L. Nasser
Assistant Examiner—Patricia C. Mallari
(74) Attorney, Agent, or Firm—Rabin & Berdo, P.C.

(57) ABSTRACT

A method and an apparatus for non-invasive blood-pressure measurement performing step-by-step inflating and deflating of the cuff pressure are disclosed. The step-by-step inflation-and-deflation process of the invention can determine the highest inflating pressure and provide enough data to obtain a curve fitting envelope. Therefore, the inflation pressure of the cuff to be pumped much higher than the normal systolic pressure of the conventional method can be prevented. A comfortable systolic and diastolic pressure determination method applying fuzzy control is achieved.

7 Claims, 3 Drawing Sheets

METHOD AND APPARATUS FOR NON-INVASIVE BLOOD-PRESSURE MEASUREMENT

CROSS-REFERENCE TO RELATED APPLICATION

This application makes reference to and incorporates Taiwan patent application Serial No. 89117855, filed Sep. 1, 2000.

BACKGROUND OF THE INVENTION

1. Field of Invention

The present invention relates in general to an oscillometric non-invasive method and apparatus for measuring blood pressure, and more particularly to a method and apparatus which perform a step-by-step inflation and deflation of a pressure cuff for a comfortable systolic and diastolic pressure determination.

2. Description of Related Art

The heart of a human being is like a pump, and the muscles of the heart periodically contract to force blood through the arteries of the human. As a result, irregularly-shaped pressure pulses exist in theses arteries and cause them to flex or oscillate. The base line pressure for these pulses is known as the diastolic pressure and the peak pressure for these pulses is known as the systolic pressure. A further pressure value, known as the "mean arterial pressure" (MAP), represents a time-weighted average of the blood pressure.

In the past, various techniques and devices have been used for measuring one or more of these blood pressure values. The most common method involves applying a pressure cuff about the upper arm of the human and inflating it so as to stop the flow of blood in the brachial artery. The pressure is then slowly relieved while a stethoscope is used on the distal portion of the artery to listen for pulsating sounds, known as Kortotkoff sounds, that accompany the reestablishment of blood flow in the artery. As the pressure in the cuff is reduced further, the Korotkoff sounds eventually disappear. The cuff pressure at which the Korotkoff sounds first appear during deflation of the cuff is a measure of the systolic pressure and the pressure at which these sounds disappear is a measure of the diastolic pressure. This method of blood pressure detection is generally known as the "auscultatory method".

Various devices are well known in the prior art for automatically performing blood pressure measurement by the auscultatory method. These devices employ a pump to automatically inflate a pressure cuff and a microphone to convert the Korotkoff sounds into electrical signals which are easily detected by various types of circuits. Other techniques have also been used to detect blood pressure from outside the subject's body, e.g., via Doppler shifts in ultrasonic waves reflected by the artery wall. In addition, there are intrusive devices that are inserted directly into the blood vessels for measurement of the pressure. However, the most commonly used method for measuring blood pressure, other than the auscultatory method, is the "oscillometric method".

The oscillometric technique is based on the fact that the pumping of blood through the arteries by the heart causes the arteries to flex. Even in the area adjacent to or within a pressure cuff applied to the arm of a human, these pressure variations exist. In fact, the pressure variations will pass from the artery through the arm of the human with attenuation and into the pressure cuff itself. While these pressure variations are small compared to the typical pressure applied by the cuff, they are nevertheless detectable by a transducer located to measure the pressure within the cuff. It has been found that these pulses, called "complexes," have a peak-to-peak amplitude which is minimal for applied cuff pressures above the systolic pressure and below the diastolic pressure. The amplitude of these complexes, however, rises to a maximum value. Physiologically, the cuff pressure at this maximum value approximates the MAP. It has further been found that the complex amplitudes of cuff pressures equivalent to the systolic and diastolic pressures have a fixed relationship to this maximum value. Thus, the oscillometric method is based on measurements of detected complex amplitudes at various cuff pressures.

However, the above-mentioned oscillometric method has drawbacks. One is that the inflation pressure of the cuff must to be pumped much higher than the normal systolic one. For example, the pressure is generally about 180 mmHg to 240 mmHg for ensuring the detection of the blood pressure value in specific cases of high blood pressure. Users thus always suffer from uncomfortable measurement while the cuff is inflated for a period of time. The continuous contraction of the cuff will cause pain, especially for obese people, and even further harm. On the other hand, the conventional measuring technique is ineffective because the normal systolic pressure is around 130 mmHg and the much higher inflation pressure is needed in case of an exception.

SUMMARY OF THE INVENTION

Therefore, it is an object of the present invention to provide a method and an apparatus for performing comfortably and accurately oscillometric blood-pressure measurement.

According to the above object, the blood pressure determining method includes, (a) applying pressure to occlude the artery of a subject; (b) reducing the pressure to permit an increasing flow through the progressively less occluded artery; (c) monitoring arterial counterpressure oscillations at each pressure reducing step; (d) converting the counterpressure oscillations to voltage signals; (e) processing the voltage signals into a sequence of peak amplitudes to obtain a curve; (f) repeating the steps from applying pressure to obtaining a curve until at least two curves, enough for curve fitting an oscillometric envelope, are obtained, and a highest artery occluded pressure is higher than a predetermined value plus a mean arterial pressure determined by one of the curves; and (g) computing a systolic and a diastolic pressure based upon the envelope.

In another aspect, the blood pressure determining apparatus includes, (a) an inflatable and deflatable cuff; (b) controlling means, for controlling cuff pressure so as to perform a step-by-step inflating and deflating of the cuff until a maximum cuff pressure is higher than a predetermined value plus a mean arterial pressure detected for a subject; (c) a monitoring means, for monitoring arterial counterpressure oscillations at each of the cuff pressure deflating processes, a pressure transducer, a processor and a calculator; (d) a pressure transducer means, coupled to the cuff for converting the counterpressure oscillations to voltage signals; (e) a processing means, for processing the voltage signals into a sequence of peak amplitudes at each pressure deflating process, the sequence lying along a curve, and at least two curves, enough for curve fitting an oscillometric envelope, being obtained according the step-by-step inflation-and-deflation process; and (f) a determining means, for determining a systolic and a diastolic pressure based upon the envelope.

Wherein the curves includes an ascending curve, a maximum curve and a descending curve in a graph of oscillation amplitudes. The predetermined value is about 20 mmHg to about 40 mmHg.

The scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become fully understood from the detailed description given hereinbelow for illustration only, and not for limitation of the present invention, and wherein.

DETAILED DESCRIPTION OF THE INVENTION

Figure 1:
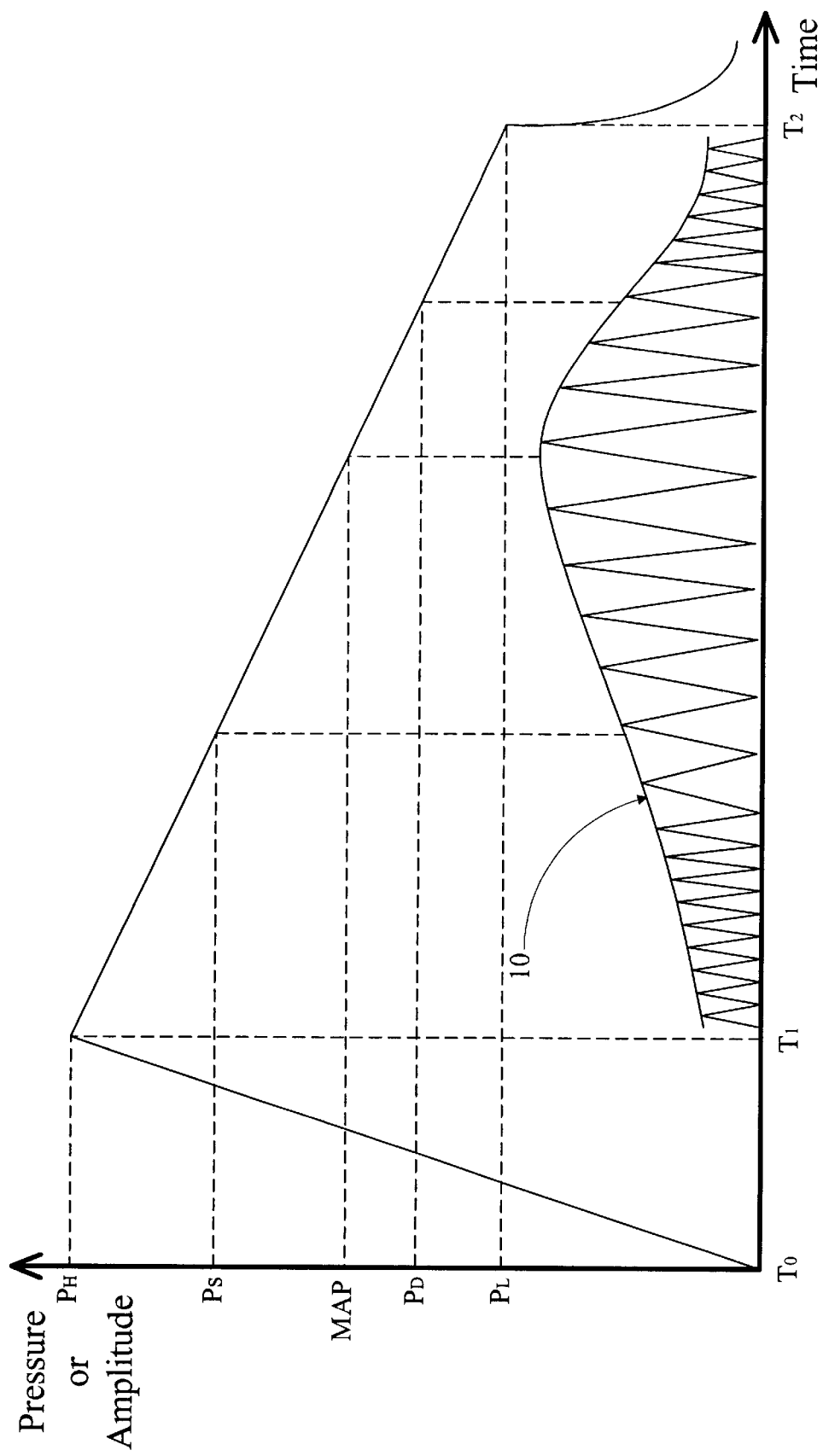
FIG. 1 shows two superimposed graphs of cuff pressure versus time and oscillation amplitudes versus time respectively according to the conventional method.

Referring to FIG. 1, the upper graph illustrates a typical cuff pressure/time graph of an oscillometric method of measuring blood pressure. At a time $T_0$, the pressure cuff which is applied to a subject's limb containing an artery, such as a human being's arm, is inflated to the pressure $P_H$ (above the systolic pressure $P_S$), thereby occluding the artery. The highest $P_H$ value at a time $T_1$, in general, is selected to be much higher than a normal $P_S$ value, such as 180 mmHg or above, to ensure that the blood-pressure measuring device can be available for all users; otherwise, a patient with hypertension may suffer from miss-detection of his blood pressure. Next, during the time $T_1$ to $T_2$, the cuff pressure is deflated to permit an increasing flow through the progressively less occluded artery and at each pressure the arterial counterpressure oscillations are monitored. Accordingly, the cuff pressure complexes are measured after such pulses begin. After suitable filtering and amplification, corresponding oscillation peaks are obtain and depicted as an envelope 10 of the lower graph of FIG. 1, which illustrates a typical oscillation amplitude/time graph. As deflating of the cuff continues, the oscillation peak amplitudes will normally increase from a lower level to a relative maximum and, thereafter, will decrease. The cuff pressure at which the amplitude has a maximum value is normally representative of the mean arterial pressure (MAP). Finally, at the time $T_2$, the pressure $P_L$ is reduced below the diastolic pressure $P_D$. Usually the $P_L$ value is sufficiently lower than a normal $P_D$ value, and the cuff is then entirely deflated to finish the whole measurement.

Prior improvements in the oscillometric measurement technique always focused on how to accurately obtain the counterpressure oscillations during the cuff deflation process, and different calculation approaches to determine the systolic and diastolic pressure according to the mean arterial pressure. However, all of the prior methods for inflating the cuff are based on a consideration of the systolic pressure. Therefore, they cannot properly solve the discomfort patients experience while blood pressure is being measured.

Figure 2:
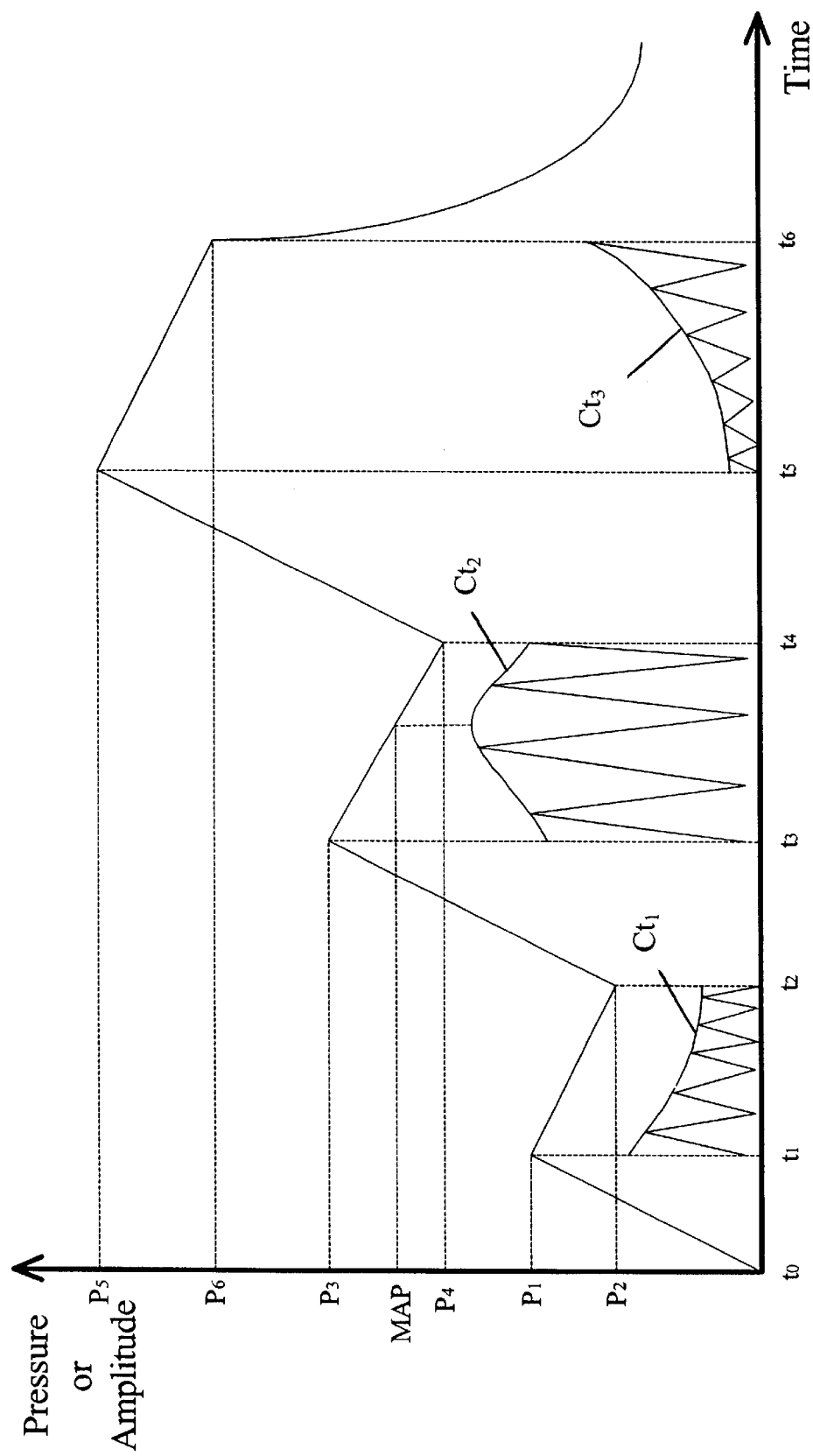
FIG. 2 shows two superimposed graphs of cuff pressure versus time and oscillation amplitudes versus time respectively demonstrating the present invention.

In comparison, please turn to FIG. 2, a step-by step inflating and deflating of the cuff is performed in the present invention, which permits a comfortable blood-pressure measurement. In this embodiment, there are three inflation-and-deflation cycles or processes. In a first step, with respect to the time interval from $t_0$ to $t_2$, the pressure cuff is inflated to $P_1$ at time $t_1$, and then deflated to $P_2$. The purpose of this step is to obtain a curve $Ct_1$ containing the diastolic pressure point from corresponding sequence of peak amplitudes enveloped by the above-mentioned complexes monitoring. The curve $Ct_1$ can be regard as the portion of the descending curve closest to $T_2$ of the envelope 10 in FIG. 1. In a second step, with respect to the time interval $t_2$ to $t_4$, the cuff is continuously inflated from $P_2$ to $P_3$, which is higher than $P_1$ at a time $t_3$, and then it is deflated to $P_4$. It is preferred to obtain a curve $Ct_2$, which corresponds to the maximal portion of the curve at the middle section of envelope 10 in FIG. 1 and which contains the MAP point. Therefore, the mean arterial pressure can be calculated according to $Ct_2$. More important, the present invention is dependent on the MAP to determine the inflating cuff pressure in the third step. In the third step, with respect to the time interval $t_4$ to $t_6$, the cuff is inflated to a pressure level equal to MAP plus a predetermined value, thus reaching the highest cuff pressure $P_5$. After that, during the deflation process from $t_5$ to $t_6$, a curve $Ct_3$ is preferably obtained containing the systolic pressure point and the measurement is then finished.

Figure 3:
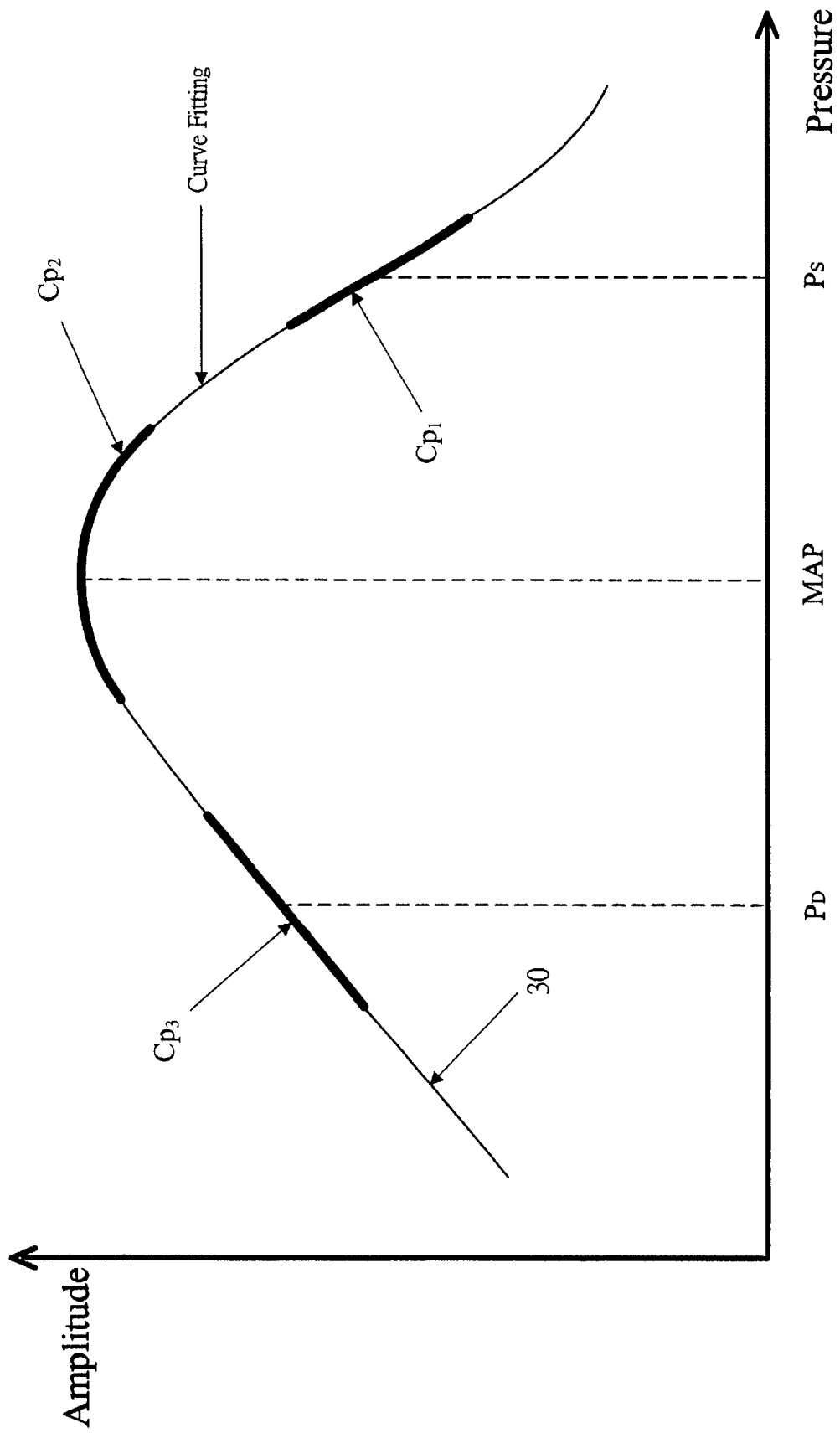
FIG. 3 is a graph of oscillation amplitudes versus cuff pressure and a curve fitted thereto with respect to FIG. 2.

Please refer to FIG. 3, a graph of oscillation amplitudes versus cuff pressure. Bold curves $Cp_1$, $Cp_2$ and $Cp_3$ corresponding to the $Ct_1$, $Ct_2$ and $Ct_3$ curves respectively in FIG. 2 are illustrated. An envelope 30 is obtained by a curve fitting of the curves $Cp_1$, $Cp_2$ and $Cp_3$. It is clear that the systolic $P_S$ and diastolic $P_D$ can be thus determined by the curve-fitting envelope 30 according to prior art calculations.

The characteristic of the present invention is quite different from the prior blood-pressure determination because the measuring of systolic pressure in FIG. 1 cannot be predicted; therefore, the predetermined highest inflating cuff pressure must be fixed to a much higher value than the normal systolic pressure. However, for a majority of people the systolic pressure is around 130 mmHg, even though the prior method always inflates the cuff to a pressure of 180 mmHg or above. It causes an uncomfortable measurement even if the inflation is applied rapidly. Moreover, it is not suitable for repeated measurements in view of the fatigue of the occluded blood vessel; the measurement may be incorrect. The highest inflating cuff pressure $P_5$ of the present invention depends on the MAP. According to the relationship between the MAP and the systolic pressure, the $P_5$ is equal to MAP plus a predetermined value such as about 20 mmHg to about 40 mmHg. For most users their MAP is around 110 mmHg, so the maximum value of the inflation pressure in the present invention is merely around 140 mmHg to accomplish the measurement. Accordingly, during the measuring process, the invention predicts the systolic pressure by reference to the MAP and thus determine the highest inflation pressure. In FIG. 2 and FIG. 3, the curve $Ct_2$ with respect to $Cp_2$ has the maximum value and the MAP must be obtain during the step-by-step inflation and deflation process of the invention. For this preferred embodiment, the descending curve $Ct_1$ with respect to $Cp_1$, in first interval of $t_1$ to $t_2$, employs a first inflation pressure $P_1$ that is lower than the MAP. For other cases, maybe the curve $Ct_1$ ($Cp_1$) is obtained in the first step, and then the cuff is inflated to the highest pressure, and thereafter it is preferably deflated to a sufficiently lower value so that the diastolic pressure can be obtained. Furthermore, in this preferred embodiment, the curve $Ct_1$ ($Cp_1$) exactly contains the diastolic pressure and the curve $Ct_1$ ($Cp_1$) contains the systolic pressure; however, it may be not happened every time in practice and will not influence the measurement whatever. The step-by-step inflation-and-deflation process of the present invention is for determining the highest inflating pressure and providing enough data to obtain the curve fitting envelope 30. The systolic and diastolic pressure is actually calculated according to the envelope 30. If the precise portions of the curves that are shown are reached, the curve fitting envelope can be more accurate.

Finally, an apparatus for measuring blood pressure according to the method of the present invention is provided. The apparatus includes an inflatable and deflatable cuff, a controller, a monitor, a pressure transducer, a processor and a calculator. The controller is used for controlling the cuff pressure so as to perform a step-by-step inflating and deflating of the cuff until a maximum cuff pressure is reached that is higher than a predetermined value plus a mean arterial pressure that has been detected for a subject. The monitor detects arterial counterpressure oscillations at each of the cuff pressure deflating processes. The pressure transducer is coupled to the cuff for converting the counterpressure oscillations to voltage signals. Next, the processor is used for processing the voltage signals into a sequence of peak amplitudes at each pressure deflating process, the sequence being enveloped by a curve. At least two curves (enough for curve fitting an oscillometric envelope) are obtained according the step-by-step inflation-and-deflation process. The calculator then computes a systolic and a diastolic pressure based upon the envelope.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A method for measuring blood pressure, comprising the steps of:
   (a) applying pressure to an artery of a subject;
   (b) reducing the pressure to permit an increasing flow of blood through the artery;
   (c) monitoring arterial counterpressure oscillations while step (b) is conducted;
   (d) converting the counterpressure oscillations to voltage signals;
   (e) processing the voltage signals into a sequence of peak amplitudes that define a curve;
   (f) repeating steps (a) through (e) to obtain at least one further curve;
   (g) fitting the curves to an oscillometric envelope; and
   (h) finding at least one blood pressure value from the oscillometric envelope.

2. The method as set forth in claim 1, further comprising finding a mean blood pressure value from one of the curves, and wherein the highest pressure applied in step (a) and the at least one repetition thereof is the mean blood pressure plus a predetermined value.

3. The method as set forth in claim 2, wherein the predetermined value is about 20 mmHg to about 40 mmHg.

4. The method as set forth in claim 1, wherein the curves include an ascending curve, a curve having a maximum, and a descending curve.

5. The method as set forth in claim 1, wherein the at least one blood pressure value found in step (h) includes the systolic blood pressure.

6. The method as set forth in claim 1, wherein the at least one blood pressure value found in step (h) includes the diastolic blood pressure.

7. The method as set forth in claim 1, wherein the pressure applied in step (a) and the pressure applied in each at least one repetition thereof are different.

* * * * *